United States Patent
Salin et al.

(10) Patent No.: US 11,684,721 B2
(45) Date of Patent: Jun. 27, 2023

(54) APPARATUS AND METHOD FOR MEASURING AND RECORDING THE QUANTITY OF MEDICAMENT REMAINING IN A MEDICAMENT DOSING DEVICE

(71) Applicant: SALECRON OY, Joensuu (FI)

(72) Inventors: Eero Salin, Joensuu (FI); Kari Leinonen, Joensuu (FI)

(73) Assignee: SALECRON OY, Joensuu (FI)

( * ) Notice: Subject to any disclaimer, the term of this patent is extended or adjusted under 35 U.S.C. 154(b) by 248 days.

(21) Appl. No.: 16/956,643

(22) PCT Filed: Dec. 21, 2018

(86) PCT No.: PCT/FI2018/050961
§ 371 (c)(1),
(2) Date: Jun. 22, 2020

(87) PCT Pub. No.: WO2019/122531
PCT Pub. Date: Jun. 27, 2019

(65) Prior Publication Data
US 2020/0405966 A1    Dec. 31, 2020

(30) Foreign Application Priority Data
Dec. 22, 2017 (FI) .................................... 20176160

(51) Int. Cl.
*A61M 5/315* (2006.01)
*A61M 5/00* (2006.01)
*A61M 5/31* (2006.01)
*G01F 23/292* (2006.01)

(52) U.S. Cl.
CPC ........ *A61M 5/31535* (2013.01); *A61M 5/002* (2013.01); *A61M 2005/3126* (2013.01); *A61M 2205/3306* (2013.01); *A61M 2205/6081* (2013.01); *A61M 2205/8262* (2013.01); *G01F 23/292* (2013.01)

(58) Field of Classification Search
CPC .............. A61M 5/31535; A61M 5/002; A61M 2005/3126; A61M 2205/3306; A61M 2205/6081; A61M 2205/8262; G01F 23/292
See application file for complete search history.

(56) References Cited

U.S. PATENT DOCUMENTS

2007/0287959 A1* 12/2007 Walter .................... A61M 1/63
                                                          604/131
2009/0229374 A1*  9/2009 Carlisle ..................... G01F 1/28
                                                          73/514.05

* cited by examiner

*Primary Examiner* — Tasnim Mehjabin Ahmed
(74) *Attorney, Agent, or Firm* — Mark M. Friedman

(57) ABSTRACT

The present invention concerns an apparatus (1) for measuring and recording the remaining quantity of medicament in a medicament dosing device (2). The apparatus (1) has a location where the medicament dosing device (2) can be inserted. Combined with that location the apparatus (1) has equipment for measuring and analysing. The apparatus is characterised in that this equipment for measuring and analysing comprises a contact image sensor (3) combined with that location for the medicament dosing device, and a software in connection with the contact image sensor. In addition the object of this invention is the corresponding method for measuring and recording the remaining quantity of medicament in a medicament dosing device (2).

9 Claims, 6 Drawing Sheets

Figure 1:
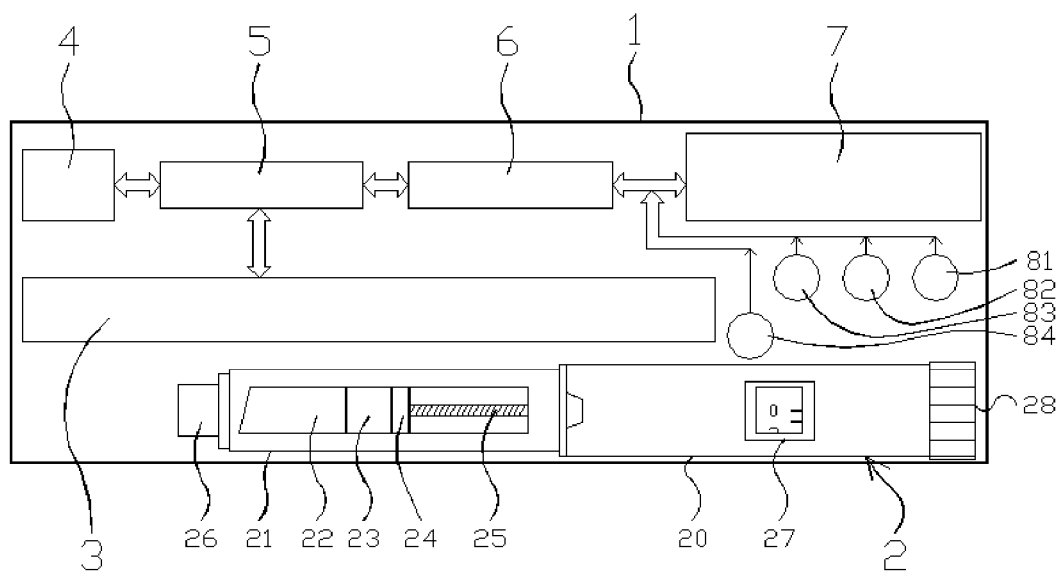

```
OUTPUT DOSES: Transfer -> Capture Text...
File:  Type  FileName.csv   or  Browse...
Press  Start  and  Enter date     ,Day,Time ,ID,  Dose, left,  error
2017-08-07,MON,10:18,NR,   6.2,293.8,   0.5
2017-08-07,MON,10:25,NR,   8.9,284.9,   0.5
2017-08-07,MON,13:33,NR,   2.0,282.9,   0.5
2017-08-07,MON,16:43,NR,   7.6,275.3,   0.4
2017-08-07,MON,22:06,NR,  11.9,263.4,   0.3
2017-08-08,TUE,10:25,NR,   9.3,254.1,   0.4
2017-08-08,TUE,13:33,NR,   1.7,252.4,   0.5
2017-08-08,TUE,16:43,NR,   4.9,247.5,   0.4
2017-08-08,TUE,22:06,NR,   7.3,240.2,   0.4
2017-08-09,WED,10:25,NR,  13.9,226.3,   0.5
2017-08-09,WED,13:33,NR,   2.1,224.2,   0.4
2017-08-09,WED,16:43,NR,   6.3,217.9,   0.4
2017-08-09,WED,22:06,NR,   7.9,210.0,   0.3
2017-08-10,THU,10:25,NR,  11.5,198.5,   0.4
2017-08-10,THU,13:33,NR,   2.3,196.2,   0.4
2017-08-10,THU,16:43,NR,   5.1,191.1,   0.4
2017-08-10,THU,22:06,NR,   7.2,183.9,   0.5
2017-08-11,FRI,10:25,NR,  13.7,170.2,   0.5
2017-08-11,FRI,13:33,NR,   1.9,168.3,   0.5
2017-08-11,FRI,16:43,NR,   7.7,160.6,   0.4
2017-08-11,FRI,22:06,NR,   7.7,152.9,   0.4

Transfer -> Capture Text... -> Stop
```

Fig. 7

APPARATUS AND METHOD FOR MEASURING AND RECORDING THE QUANTITY OF MEDICAMENT REMAINING IN A MEDICAMENT DOSING DEVICE

The present invention concerns a method for measuring, recording and monitoring the dose delivered by a medicament dosing device, in particular by a pen-injector type delivery device, and further in particular by an insulin pen, and an apparatus to realize the method. In particular relates the present invention to measuring the injected dose reliably and accurately enough especially for insulin used in self care of diabetes.

It is estimated that 425 million adults around the world have diabetes, half of them undiagnosed (diabetesatlas.org). In Finland about half a million people live with diabetes (Finnish Diabetes Association), which means that one out of ten has diabetes. 15 percent of Finland's health care expenditure constitutes of the costs of the care provided for people having diabetes (Finnish Diabetes Association). Injection from a syringe is the most common daily care for diabetes today and in the foreseeable future.

Still most of diabetes patients keep records of their injections in a paper notebook. The patient can write the doses incorrectly or inaccurately or very often afterwards from vague recollections. There are also many diabetics with no dose recording at all. Additionally, the patient may intentionally cheat by making false records to prove his good self-care or to please the doctor.

The patient or the doctor monitors the blood glucose levels and the insulin doses, and from the combination of them, deduce the best insulin doses for future dispenses. Reliable data helps to maintain blood glucose as uniform as possible. Wrong data jeopardizes the treatment program, possibly even endangering the patient's life. In this application the value of keeping electronic medical records in place of paper records has been widely understood more than twenty years. With a well acting system the electronic recording should be reliable and accurate. Combining dose records with blood glucose readings, the electronic system can calculate for instance the insulin sensitivity or even suggest the most suitable insulin dose for a certain point of time of day or week taking into account the newly measured blood glucose value.

Because many users of insulin pens have memory disorder, the need for reliable automatic dose recording is evident.

Furthermore, the accuracy of the measurement of the insulin dose must be sufficient. With diabetes patients using injectable insulin, the blood glucose balance and the needed insulin dose can be controlled with an uncertainty of ±2 iu (international unit, 1/100 ml). In the injection device meant for adults, the resolution of the dose is 1 iu. For children one dose snap is 0.5 iu with rapid insulin and 1 iu with long-acting insulin. ISO standard 11608-1:2012 requires the following accuracy from insulin pens: the error for a dose of 1 iu is allowed to be at most ±1 iu, the error for a dose of 40 iu is allowed to be at most ±2 iu, and the error for a dose of 80 iu is allowed to be at most ±4 iu. As a result, a measurement accuracy of about ±0.5 iu should be sufficient in most cases.

Several attempts have been made to realize a good electronic dose measurement and recording system for self-care of diabetes. The system described in U.S. Pat. No. 5,176,502 measures the position of the plunger of an insulin pen electrically with a linear potentiometer engaged to the plunger rod. The dose and the injection date and time are stored in the memory of the device. The realized system is integrated into an insulin pen and makes the insulin pen large in size.

U.S. Pat. No. 4,950,246 describes a system that delivers the injection fluid using an electric stepper motor. The dose information is stored according to the steps of the stepper motor.

Further U.S. Pat. No. 5,593,390 describes a system built into an insulin pen. The goal of it is to measure and record the dose from a refillable injection device or more accurately from an insulin pen. The used method calculates the dose by measuring the rotation of the dose adjustment knob. Using the insulin pen is quite normal. Publication JP 2000-237309 presents a very similar device which is integrated into an insulin pen. It also records and monitors insulin doses and injection dates and times. The exact moment of actual injection is found out with an electric loop from the injection needle through the body of the patient back to the finger on the dosing knob. The dose is measured from the rotation of the knob.

The systems built into the insulin pen constitute a challenge because the described system or modification should be realized into every injection device in use, also into pre-filled, disposable injection devices, that patients often use. The additional parts make the price of the disposable pen too high in continuous use.

The method of U.S. Pat. No. 5,792,117 uses colour marking along the plunger rod of the injector device and a separate housing for the electronics. The injection dose is measured by watching the position of the plunger relative to an optical point-sensor that is located in the separate housing, which has a slot for receiving and aligning the injection device for dose measurement. The injection device must have a colour band that changes its colour linearly along the plunger rod. The optical sensor measures the colour at that point and calculates the position of the plunger. The injection device must be accurately located in the correct position, because the reference point for the measurement resides in the housing. In addition, the plunger rod of the injection device must have a colour band, which of course does not exist in the insulin pens in the market.

U.S. Pat. No. 5,720,733 describes a method for measuring the injected dose using a capacitive element included in the syringe. Similarly, U.S. Pat. No. 5,782,814 describes a method for measuring the injected dose using an inductive technique. The plunger has an iron core which changes the inductance of a coil in the receptacle. Neither of these techniques is suitable for practical insulin pens.

Publication AU 2011231697 B2 presents an invention, which aims to measure and record the medicament dose ejected from a pre-filled disposable injection device, or more accurately, from an insulin pen. In this embodiment a sensor/data processing/display apparatus is attached on the upper part of the insulin pen. This apparatus is releasably attachable without causing any damage to the medical device or the apparatus. The apparatus uses a tiny camera located on the dose display of the injecting device for capturing an image of the display. The data processor uses pattern or character recognition to transform the image to a numerical value of the display reading. In addition, the apparatus uses at least one acoustical sensor, a microphone, to listen to the sounds from using the injection device. According to the acoustical information the apparatus determines when the reading on the display represents the dose to be injected. With this camera or with a second, optional, optical sensor the apparatus measures the colour of the body of the injection device and concludes the type of the medicament. There are some uncertainties related in this method, and therefore the user is advised to check and possibly correct the dose values with a button. The apparatus could as well reside in a separate housing, which causes an extra step in using the injection device: after setting the dose to be injected, the injection device must be put back to the housing for reading the dose, and only after that the injection can be done. This is a trick that nobody wants to do in practice. This method is suitable for disposable insulin pens, because no modification is needed to the pen itself. However, extra working steps are needed either with attaching and releasing the apparatus on the injection device or with carrying the injection device back and forth to its housing. The apparatus on an insulin pen also makes the pen large and clumsy. Acoustical analysis and dose correction with a user button don't sound very reliable.

Patent application publication US 2015/0144793 describes a system which has a plurality of light sources and sensors located along the container of a drug delivery device. The physical apparatus consists of a tube that holds typically eight light sources and eight sensors opposite to each other. The drug delivery device will be pushed inside the tube between the light sources and the sensors. The light is thus radiated through the liquid in the container and reflected from the ends of the plunger and also from many other objects. By analysing the typical responses of each light sensor, the position of the plunger is found out, and further the remaining quantity of the liquid in the container can be calculated.

Publication EP20120838934 (EP2764882) describes a motorized injection device that has a memory to store a planned cumulative pharmaceutical dose and actual doses, and a software to supervise and compare the injection schedules and correct the planned injection doses. The apparatus does not include any equipment for direct dose measurement.

The known methods and apparatus listed above have a common target to measure and record the injection times and the doses injected from an injection syringe, specially thinking about injections made by diabetes patients as self care.

In the known apparatus and methods, extra parts must be built or changes must be made into the injection device or particularly into the insulin pen. In a part of the known solutions, the usage of the injection device requires extra steps and thus complicates the usage of the injection device.

In addition, to realize an appropriate self care of diabetes, the apparatus should be as inconspicuous as possible to the user, so that the apparatus takes care of all of its functions spontaneously and automatically without user intervention. The apparatus should show the injection date and time, the type of the injected medicament, the injected dose and the quantity of the medicament remaining in the syringe automatically after every injection.

The foregoing problems are solved with an apparatus according to patent claim 1 and with a method according to patent claim 12.

The preferred embodiments of the invention are presented in dependent claims.

The present invention concerns an apparatus for measuring and recording a medicament dose remaining in a medicament dosing device that has a liquid container that contains the medicament to be dispensed, a plunger movably positioned inside the liquid container, and an injection end through which the medicament is expelled out from the liquid container, and which apparatus has a location where the medicament dosing device can be inserted, and combined with that location, equipment for measuring and analysing. The apparatus according to this invention is characterized in that the equipment for measuring and analysing comprises a contact image sensor combined with that location for the medicament dosing device, and a software in connection with the contact image sensor.

The apparatus according to this invention has advantageously electronics and/or a power supply. The apparatus according to this invention may further have a lid that functions as a switch for the supply voltage, which is advantageously taken from an internal power supply of the apparatus or from an external power supply coupled to the apparatus.

In a preferred embodiment of this invention, the contact image sensor can be used to capture a longitudinal, advantageously one or more pixels wide image, or in other words a colour curve, of the medicament dosing device. Further on, using the contact image sensor it is possible to recognise the colour of the injection end or of the medicament container, from which colour the type of the medicament can be concluded. Furthermore the software of the apparatus has means for solving the position of the plunger of the medicament dosing device relative to the liquid container.

In an other preferred embodiment of the invention, the software of the apparatus has means for calculating and recording the quantity of the remaining medicament in the liquid container. Further on, the apparatus has means for accessing the previously recorded remaining quantity for calculating the expelled dose.

According to this invention, the apparatus may have a display for viewing the remaining quantity and the expelled dose to the user.

Moreover advantageously the medicament dosing device to be used with this apparatus is an injection syringe or an insulin pen.

Moreover advantageously the apparatus according to this invention can be realised into a storage case of the medicament dosing device, which storage case fits in pocket.

In the method according to this invention for measuring and recording the remaining quantity of the medicament in the medicament dosing device, a medicament dosing device 2 is inserted into a location inside the apparatus 1, the medicament dosing device having a liquid container that contains the medicament to be dispensed, a plunger 23 that is movably positioned inside the liquid container 22, and a dispensing end, through which the medicament is expelled out from the liquid container 22 by the aid of a plunger 23, and the apparatus 1 has a location, where the medicament dosing device can be inserted, and combined with that location, equipment for measuring and analysing. The method according to this invention is characterised in that the quantity of the medicament is measured and analysed using a contact image sensor and software.

An injection device has a cylinder containing the liquid to be dispensed, and inside the cylinder a movable plunger that expels the liquid out through the tip of the cylinder a dose set by the user at a time. The time between the injections the injection device is kept in a storage case. In this method, the storage case is equipped with electronics that measures and records the quantity of the remaining liquid in the cylinder every time when the injection device is inserted into the storage case. A contact image sensor is located in the storage case in combination with the space reserved for the injection device. This sensor captures a longitudinal one pixel wide image, or in other words a colour curve, of the injection device. From the colour curve, the software of the apparatus concludes the position of the plunger with respect to fixed parts of the injection device. From this information and the cylinder dimensions the software calculates the quantity of the remaining liquid in the cylinder. By subtracting this from the preceding quantity fetched from the memory of the apparatus, the software calculates the injected dose and views it on the display of the apparatus. The software records the date and time of the injection and the quantity of the remaining liquid in the memory. With the same contact image sensor the apparatus recognizes the colour of the end of the cylinder and concludes the type of the used liquid. The apparatus also records that in its memory.

If the user wishes, he can use the three push buttons of the apparatus to scroll the dose history. Furthermore if the user or the healthcare personnel wants, the apparatus can be connected to a personal computer with a data transfer cable for outputting the dose history. Furthermore in service mode, all information of the apparatus can be transferred and examined with a personal computer.

All the technique is embedded inside the storage case. The apparatus consumes power only when the lid of the storage case is open.

In the apparatus and method according to this invention for measuring and recording the remaining quantity in the medicament dosing device, a medicament dosing device has a cylindrical part that contains the medicament to be dispensed, and a movable plunger inside the cylinder. The plunger expels the medicament liquid out through the tip of the cylinder a dose set by the user at a time. The time between the injections the medicament dosing device is kept in a storage case that fits in pocket.

The storage case is equipped with electronics that measures and records the quantity of the remaining medicament liquid in the cylindrical part every time when the medicament dosing device is inserted into the storage case. A contact image sensor is located in the storage case beside the space reserved for the medicament dosing device. This sensor captures a longitudinal one pixel wide image, or in other words a colour curve, of the medicament dosing device. From the colour curve, the software of the apparatus concludes the position of the plunger with respect to fixed parts of the medicament dosing device. From this information and the dimensions of the cylindrical part the software calculates the quantity of the remaining liquid in the cylindrical part. By subtracting this from the preceding quantity fetched from the memory of the apparatus, the software calculates the injected dose and views it on the display of the apparatus. The apparatus records the medicament dispensing date and time and the quantity of the remaining medicament liquid in its memory. With the same contact image sensor the apparatus watches the colour of the end of the cylindrical part of the medicament dosing device and concludes the type of the used medicament liquid. The apparatus also records that in its memory.

A particular application target of this invention is insulin dosing and injecting made by diabetes patients with an insulin pen as self care. The apparatus according to this invention is suitable for both reusable and disposable injection syringes. There is no need to make any changes to the injection syringe or the insulin pen. The adjustment for different medicament dosing devices, for instance injection syringes, is made by changing the parameters in the software. The software is also capable of recognizing various types of injection devices and setting the parameters automatically. The only limitation is that at least one edge of the plunger of the injection syringe must be visible at the moment of the measurement, and that the injection device has at least one recognisable fixed object.

Using the method presented in this invention does not cause extra or difficult operational steps to the user. The apparatus takes care of all its functions spontaneously and automatically without user intervention. The apparatus views the injection date and time, the type of the injected medicament, the injected dose and the remaining quantity in the injection syringe automatically after every injection. After start-up the apparatus views the current date and time and the preceding injection dose with its date and time. If the user wishes, he can use the three push buttons of the apparatus for scrolling the dose history. Furthermore, if the user or the healthcare personnel wants, the apparatus can be connected to a personal computer with a data transfer cable for outputting the dose history. Furthermore in service mode, all information of the apparatus can be transferred and examined in a personal computer. The necessary equipment fits inside a normal storage case of an insulin pen, and is not visible outside the storage case. All the technique is embedded inside the storage case. The apparatus consumes power only when the lid of the apparatus is open.

According to tests made so far the measurement inaccuracy of the remaining medicament liquid in the insulin pen has been 0.54 iu as standard deviation and zero as an average error. This complies well with the needed measurement accuracy.

This invention is described more accurately in the attached drawings where

Figure 2:
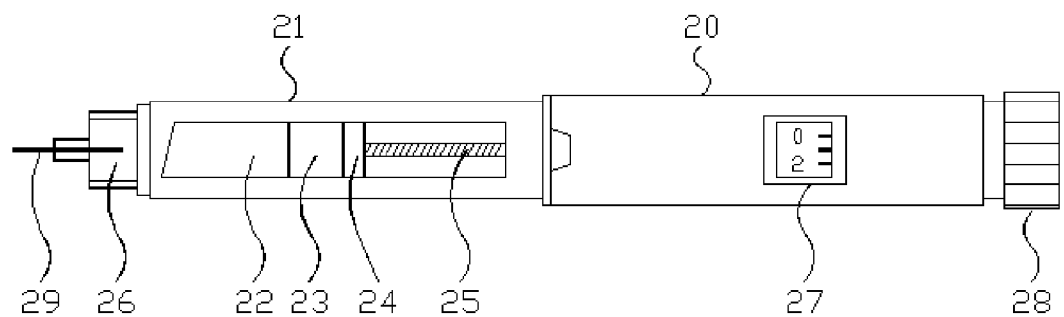
Figure 3:
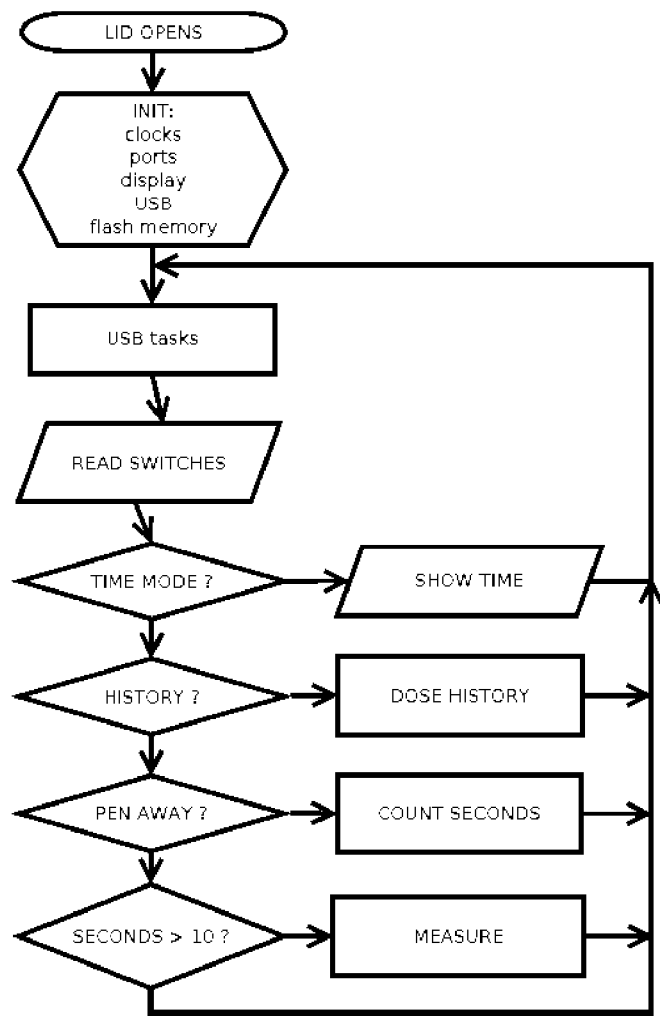
Figure 4:
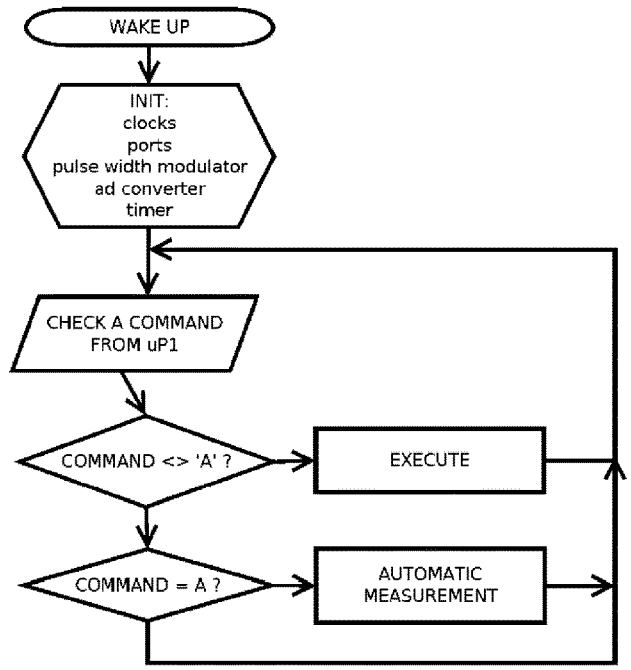
Figure 5:
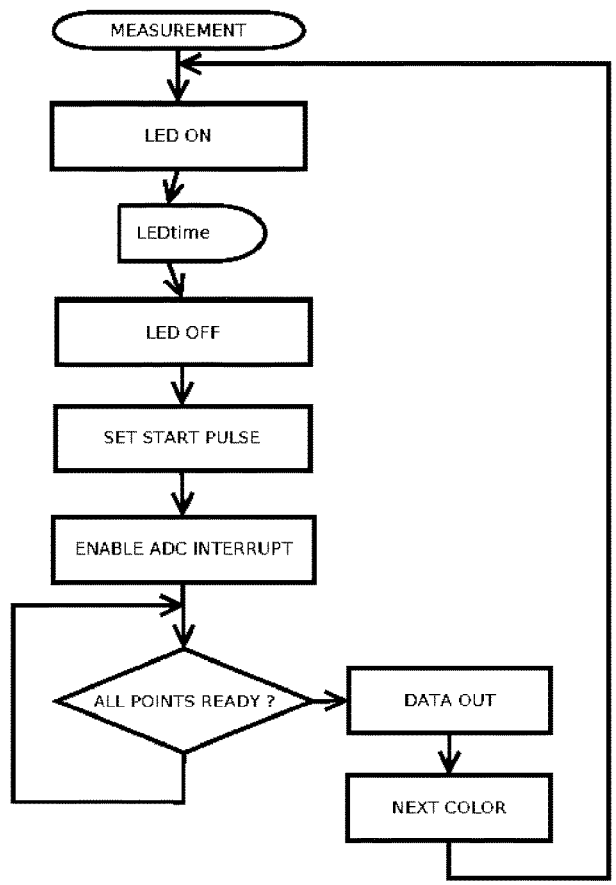
Figure 6:
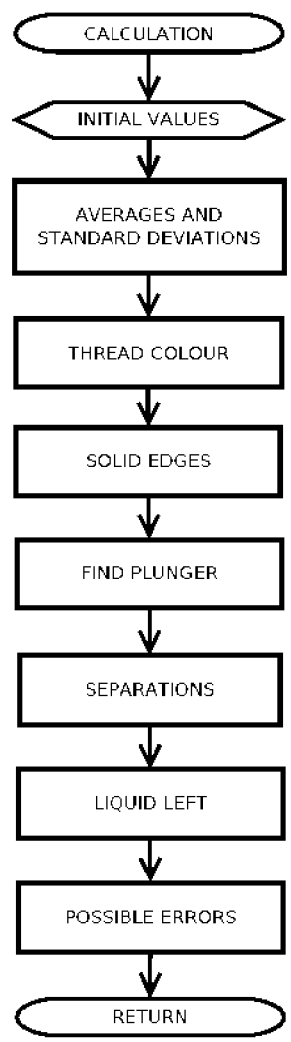
Figure 8:
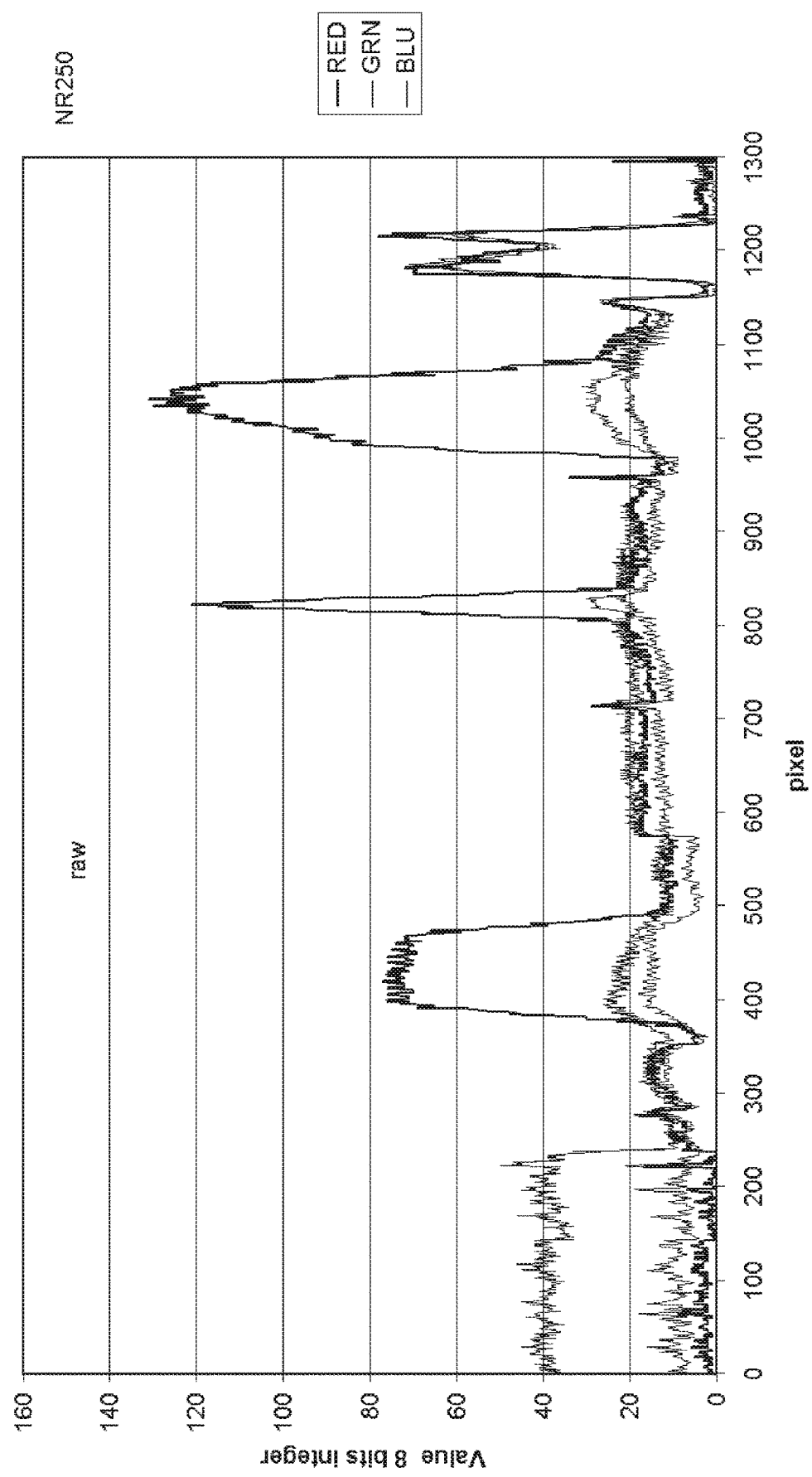

FIG. 1 presents the medicament dosing device inserted into the apparatus according to this invention and the outlines of the functional components of the apparatus in real scale;

FIG. 2 presents the medicament dosing device ready for use;

FIG. 3 presents the flow diagram of the main routine of the software of the apparatus according to this invention;

FIG. 4 presents the flow diagram of the software of the measurement processor of the apparatus according to this invention;

FIG. 5 presents the flow diagram of the measurement action according to this invention;

FIG. 6 presents the flow diagram of the dose calculation according to this invention;

FIG. 7 presents a typical output of doses to a personal computer according to this invention;

FIG. 8 presents an example of the colour curves measured by the contact image sensor of the apparatus according to this invention.

According to FIG. 2 a reusable insulin pen (the same pen can be used several years) has a stem part 20 and a container part 21 that can be separated from each other for changing the liquid container 22. At the end of the liquid container there is a screw thread 26, which has a different colour for different insulins. A disposable needle 29 is screwed on the thread for the time of injection. The liquid container has a movable plunger 23 that is pushed during the injection by the plunger rod 25 and its head 24, the rod extending out from the stem part into the liquid container. The stem part 20 holds a thread mechanism inside. The dose is set with a rotating knob 28, and the set dose is visible in the dose window 27. When the dose setting knob is rotated to the desired dose, the dose setting knob rises up at the same time. The dose is injected by pushing the dose setting knob down to the bottom. In a disposable pen the parts are the same, but the structure is entirely plastic and flimsy. The liquid container of the disposable pen can not be changed.

FIG. 1 presents the apparatus 1 according to this invention with an insulin pen 2 inserted. The insulin pen 2 is stored in the housing of the apparatus 1, when it is not being used. The lid of the housing 1 is then closed, and the power consumption of the apparatus is in practice zero. When the lid of the housing 1 is opened, the apparatus wakes up and views the current date and time and the latest injected dose and substance together with the date and time of the injection on its display 7. It is then possible to scroll the dose history using push buttons 81 to 83. When the insulin pen 2 is removed from the housing 1, the apparatus waits for the injection to happen. The user screws the needle 29 on to the thread 26 of the insulin pen, adjusts the dose with the dose adjustment knob 28 and performs the injection by pressing the dose setting knob down to bottom. After the injection the user unscrews the needle 29 from the insulin pen and inserts the pen back into the shaped location in the housing of the apparatus 1. The shaped location has some looseness in fitting, which does not affect the measurement accuracy in this method, because the reference points reside on the very same insulin pen.

When the apparatus notices that the insulin pen is stably back in its position, it performs the measurement with a contact image sensor 3. The sensor is capable of reading only grey levels, but the target is exposed with the main colours red, green and blue after each other. The final result is a longitudinal one pixel wide image with three colours, or in other words a colour curve. From that the microprocessor 6 of the apparatus concludes the positions of some fixed parts of the pen and finally the position of the plunger 23. From difference values and the dimensions of the insulin container, the processor calculates the quantity of the remaining liquid in the container. The injected dose is calculated by subtracting this quantity from the preceding quantity found in the memory.

The flow diagram of FIG. 3 presents the functions of the main routine of the user interface processor or the main processor 6. This processor 6 supervises all the functions of the apparatus. It maintains the time by the aid of its internal real time clock. It controls the display 7. It monitors the switches 81 to 84. It takes care of the traffic to the USB connector 4. It observes the presence of the insulin pen by the aid of a micro switch 84. If the insulin pen is absent at least 10 seconds, processor 6 prepares itself for making the measurement. When the pen appears stably into its position, the main processor 6 switches the measurement processor 5 active and commands it to make the measurement physically.

FIG. 4 presents the flow diagram of the main routine of the measurement processor and FIG. 5 presents the flow diagram of the measurement action. The measurement processor controls the contact image sensor 3. The contact image sensor needs pulses to control the exposing leds, a MHz class clock pulse for clocking out the analogue values of all pixels, and start and reset pulses to synchronize the clocking out. The measurement processor 5 reads the analogue values of the pixels and converts them to digital readings. At the end, the measurement processor 5 outputs all measured data to the main processor 6. After getting all the data of all three colours the main processor commands the measurement processor into sleep mode.

The main processor analyses the measured colour curves according to the flow diagram presented in FIG. 6. The main processor calculates the remaining quantity of the liquid in the container and records the quantity into its internal flash memory together with the date and time and the type of insulin. It views the injected dose and the insulin type and the remaining quantity in the container on its display 7. When the lid of the housing of the apparatus is closed, the main processor 6 shuts down its own power, maintaining only the real time clock and calendar.

If the user wishes, he can scroll the formerly injected doses together with their injection dates and times on the own display of the apparatus by using the three user push buttons 81, 82 and 83. Through the USB connection the user can output all dose history to a personal computer. An example of such an output is presented in FIG. 7.

FIG. 8 presents the measured outputs of the contact image sensor 3 in one example. The graph shows the RGB colour state of each pixel, the three individual colour channels (Red, Green, Blue) separately drawn.

With this kind of embodiment the apparatus 1 and the method for measuring work in principle with any insulin pen, also with disposable pens. There is no need to make any changes to the insulin pen, and no need to build electronics or to add extra components or a motor to the pen, which maintains the pen normal, original and handy sized.

Utilizing the method according to this invention does not require any changes to the operation of the user compared with the former. The user does not need to do anything for the apparatus, it takes care of everything spontaneously.

Most often diabetes patients use two insulin pens containing rapid insulin and long acting insulin. The software of the apparatus can separate between these two, which makes it possible to use two different pens mixed in the same apparatus. The apparatus (1) can also be built so, that two insulin pens (2) can be inserted side by side into the location of the apparatus (1).

If the insulin pen (2) must be identified with for instance a bar code, can that bar code be read with the contact image sensor (3) of the apparatus.

The reference points of the measurement reside on the insulin pen, which allows some looseness in fitting the pen into the housing of the apparatus. The apparatus measures the quantity of the remaining insulin directly by observing the position of the plunger with respect to available reference points on the insulin pen.

The apparatus (1) according to this invention utilizes a contact image sensor (3) in measuring the dose of a medicament dosing device, particularly an insulin pen. The equipment consists of the contact image sensor, the electronics and the software. In the corresponding manner can the position of the surface of any liquid or of any object be measured. By analysing the colour curves produced by a contact image sensor, it is possible to calculate the quantity of insulin and to recognise the type of the insulin. The objects on the insulin pen can be recognised and localised by searching patterns that have a correct width and a correct colour and by calculating the positions of their edges by finding the best correlation between the width and the height simultaneously.

The invention claimed is:
1. An apparatus for measuring and recording a quantity of a medicament remaining in a medicament dosing device, comprising
    a detachable medicament dosing device, having a stem part and a container part, the detachable medicament dosing device further comprising:
        a liquid container containing the medicament to be dispensed,
        a plunger residing inside the liquid container and is movable inside the liquid container with the help of a plunger head and a plunger rod,
        a screw head at the end of a liquid container that is of a different color for a different type of medicament;

a contact image sensor at a location inside the apparatus wherein the contact image sensor captures an image which is at least one pixel wide longitudinally of the detachable medicament dosing device for producing color curves;

a software of the apparatus which is in connection with the contact image sensor that concludes the position of the plunger with respect to fixed parts of the medicament dosing device;

a memory of the apparatus for storing date and time of medicament doses and the quantity of the remaining liquid in the liquid container;

a measurement processor for controlling the contact image sensor, and configured for: reading the analogue values of the pixels from the contact image sensor, converting the analogue values to digital readings data, and outputting the digital readings data;

a main processor for receiving the data from the measurement processor, analyzing the received data and calculating the remaining quantity of the liquid in the liquid container, wherein the calculation of remaining liquid in the liquid container is performed by the software which concludes the position of the plunger with respect to fixed parts of the medicament device by analyzing the color curves and the liquid container dimensions.

2. The apparatus according to claim 1, further comprising a lid that functions as a switch for the supply voltage of the apparatus, the supply voltage taken advantageously from an internal power supply of the apparatus or from an external power source connected to the apparatus.

3. The apparatus according to claim 1, wherein the detachable medicament dosing device is an injection syringe or an insulin pen.

4. The apparatus according to claim 1, wherein the contact image sensor also recognizes the color of the injection end or of the medicament container, from which color the type of the medicament can be concluded.

5. The apparatus according to claim 1, wherein the software is also capable of recognizing various types of injection devices and setting the parameters automatically.

6. The apparatus according to claim 1, wherein the software also calculates and displays injected dose by subtracting the detected quantity of remaining liquid in the container from the quantity information obtained from the memory of the apparatus.

7. The apparatus according to claim 1, wherein the main processor is connected to a micro switch that observes the presence of the medicament dosing device in the apparatus.

8. The apparatus according to claim 1, wherein the apparatus further comprises three push buttons for scrolling a history of medicament dosing.

9. A method for measuring and recording the quantity of a medicament remaining in a medicament dosing device by an apparatus, the method comprising:

inserting the medicament dosing device in an apparatus on a location, wherein
the medicament dosing device comprises:
a liquid container containing the medicament to be dispensed,
a plunger residing inside the liquid container and being movable inside the liquid container with the help of a plunger head and a plunger rod, and
a screw head at the end of a liquid container that is of a different color for a different type of medicament;

capturing at least one pixel wide image longitudinally of the medicament dosing device for producing color curves by a contact image sensor which is located inside the apparatus;

concluding the position of the plunger with respect to fixed parts of the medicament dosing device by a software of the apparatus, the software being in communication with the contact image sensor;

storing date and time of medicament doses and the quantity of the remaining liquid in the liquid container in a memory of the apparatus;

controlling the contact image sensor, and reading the analogue values of the pixels from the contact image sensor and converting them to digital readings and outputting the data by a measurement processor;

receiving the output data from the measurement processor by a main processor; and calculating the remaining quantity of the liquid in the liquid container by the main processor, wherein calculating of remaining liquid in the liquid container is performed by the software which concludes the position of the plunger with respect to fixed parts of the medicament device by analyzing the color curves information, and the liquid container dimensions.

\* \* \* \* \*